US012762705B2

(12) United States Patent
Kalayeh et al.

(10) Patent No.: US 12,762,705 B2
(45) Date of Patent: Oct. 13, 2026

(54) ULTRASOUND MOTION TRACKING TO MEASURE MOVEMENT OF STRUCTURES IN THE PELVIC AREA

(71) Applicant: REGENTS OF THE UNIVERSITY OF MICHIGAN, Ann Arbor, MI (US)

(72) Inventors: Kourosh Kalayeh, Ann Arbor, MI (US); J. Brian Fowlkes, Ann Arbor, MI (US); Bryan Sack, Ann Arbor, MI (US); William W. Schultz, Ann Arbor, MI (US); John O. Delancey, Ann Arbor, MI (US); James A. Ashton-Miller, Ann Arbor, MI (US); Payton Schmidt, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 19/073,743

(22) Filed: Mar. 7, 2025

(65) Prior Publication Data

US 2025/0308028 A1 Oct. 2, 2025

Related U.S. Application Data

(60) Provisional application No. 63/573,414, filed on Apr. 2, 2024.

(51) Int. Cl.
*G06T 7/00* (2017.01)
*A61B 8/00* (2006.01)
(Continued)

(52) U.S. Cl.
CPC ............ *G06T 7/0016* (2013.01); *A61B 8/085* (2013.01); *A61B 8/469* (2013.01); *A61B 8/5207* (2013.01);
(Continued)

(58) Field of Classification Search
CPC ......... G06T 7/12; G06T 7/0016; G06T 7/248; G06T 7/215; G06T 2207/10132;
(Continued)

(56) References Cited

U.S. PATENT DOCUMENTS

2011/0257529 A1* 10/2011 Casciaro ................ A61B 8/463 600/443
2016/0045152 A1* 2/2016 Singhal ................ A61B 8/0866 600/407

FOREIGN PATENT DOCUMENTS

WO WO-2018113282 A1 * 6/2018 ............. G06T 15/00

OTHER PUBLICATIONS

Christos E. Constantinou, "Dynamics of female pelvic floor function using urodynamics, ultrasound and Magnetic Resonance Imaging (MRI)", European Journal of Obstetrics & Gynecology and Reproductive Biology 144S (2009) S159-S165.

(Continued)

*Primary Examiner* — Boniface N Nganga
(74) *Attorney, Agent, or Firm* — MARSHALL, GERSTEIN & BORUN LLP

(57) ABSTRACT

A method of performing ultrasound motion tracking of a urethra or other pelvic floor structure includes obtaining a plurality of ultrasound images of a urethra or pelvic floor structure, identifying a reference element in the plurality of ultrasound images, and determining one or more regions of interest in the first ultrasound image including a portion of the urethra. A processor determines first and second positions, relative to the reference element, of the regions of interest in the plurality of ultrasound images. The processor further determines a change in position of the urethra from the first and second positions of the regions of interest. The processor may further determine orientations, opening, clos-
(Continued)

ing, or other movement of the urethra from the first and second positions of the regions of interest.

24 Claims, 12 Drawing Sheets

(51) Int. Cl.
*A61B 8/08* (2006.01)
*G06T 7/215* (2017.01)
*G06T 7/246* (2017.01)

(52) U.S. Cl.
CPC .............. *G06T 7/215* (2017.01); *G06T 7/248* (2017.01); *G06T 2200/24* (2013.01); *G06T 2207/10132* (2013.01); *G06T 2207/20104* (2013.01); *G06T 2207/30008* (2013.01); *G06T 2207/30196* (2013.01)

(58) Field of Classification Search
CPC ........... G06T 2207/20104; G06T 2207/30008; G06T 2207/30196; G06T 5/40; G06T 5/90; A61B 8/08; A61B 8/085; A61B 8/469; A61B 8/5207; A61B 8/5223
USPC .......................................... 600/587, 588, 591
See application file for complete search history.

(56) References Cited

OTHER PUBLICATIONS

Jones et al., “Mechanisms of Pelvic Floor Muscle Function and the Effect on the Urethra during a cough”, European Association of Urology 57 (2010) 1101-1110.

* cited by examiner

Urethral Motion Trajectory

Urethral Motion Vector

Urethral Rotation

Urethral Mobility "Report"

| | Proximal | Mid | Distal |
|---|---|---|---|
| Motion Vec. Mag. | 1.2 cm | 0.6 cm | 0.2 cm |
| Motion Vec. Direction | 18° | 28° | 49° |
| Rotation | 31° | 39° | 31° |
| Initial x-Coord. | -0.3 cm | 0.2 cm | 0.3 cm |
| Inital y-Coord | 1.9 cm | 1.1 cm | 0.2 cm |
| x-Disp. | 1.2 cm | 0.5 cm | 0.2 cm |
| y-Disp. | -0.4 cm | -0.3 cm | -0.2 cm |

ULTRASOUND MOTION TRACKING TO MEASURE MOVEMENT OF STRUCTURES IN THE PELVIC AREA

CROSS-REFERENCE TO RELATED APPLICATIONS

This application claims the benefit of U.S. Provisional Application No. 63/573,414 filed Apr. 2, 2024, the entire contents of which are incorporated herein by reference in their entirety.

STATEMENT OF GOVERNMENT SUPPORT

This invention was made with government support under DK122379 awarded by the National Institutes of Health. The government has certain rights in the invention.

FIELD OF THE DISCLOSURE

The invention generally relates to methods and systems for ultrasound tracking, and more particularly, for ultrasound motion tracking of pelvic floor structures including urethral mobility.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Monitoring and tracking of motion of internal organs is used across a range of applications such as in surgery, medical diagnostics, disease monitoring and diagnosis, fertility tracking and monitoring, and performing biological and psychological research among other applications. Ultrasound imaging is a common modality for performing imaging of organs and tissues in a patient. Ultrasound imaging typically requires an expert to physically manipulate a probe or sensor to properly capture images of target tissues and organs. Moving the ultrasound probe or sensor according to real time movements of organs of a patient is often difficult and can result in capturing images that are not usable, or prevent adequate images for observing the motion of an organ or tissues over time. Inaccurate or unusable images further prevent the use of ultrasound imaging for tracking organs for further diagnosis and treatment of diseases and conditions.

Two such conditions that may be monitored using ultrasound technologies are stress urinary incontinence (SUI), and pelvic organ prolapse (POP). SUI is characterized by involuntary urine leakage during activities that increase intra-abdominal pressure (IAP), such as coughing, sneezing, or exercising. SUI predominantly impacts women and significantly affects their quality of life, impacting social, psychological, occupational, and sexual well-being. SUI is primarily attributed to the weakening of pelvic floor muscles and the urethral sphincter, leading to diminished support for the bladder neck and urethra. Pelvic organ prolapse occurs when the bladder, vagina, uterus, and/or rectum move abnormally downward herniating through the pelvic floor.

Understanding and quantifying the dynamics of pelvic floor and urethral support is pivotal in SUI management. For over a century, abnormal urethral support has been recognized as a crucial factor in etiology and treatment outcomes of SUI and abnormal movement of the pelvic organs is the essential nature of POP. Traditional diagnostic approaches, such as clinical assessments and urodynamic studies, face limitations due to their invasive or uncomfortable nature and have limited precision. In contrast, ultrasound imaging presents a non-invasive alternative, allowing real-time visualization of pelvic floor, pelvic organs, and bladder neck movements. However, despite its advantages, ultrasound effectiveness in SUI diagnosis is limited by the subjective nature of manual image interpretation and observer variability.

Furthermore, precise measurement of pelvic floor movements are limited. Although there are established recommendations for techniques to measure urethral support, significant variation still exists across the field of how urethral support should be monitored and measured.

SUMMARY OF THE INVENTION

Techniques and systems are provided for performing ultrasound motion tracking of a urethra, pelvic organs, and floor. In an implementation, a method for performing ultrasound machine vision motion tracking of pelvic floor structures, with the specific example of tracking of a urethra, is disclosed. The method includes an ultrasound sensor or probe obtaining a plurality of ultrasound images of a region of tissue including a portion of a pelvis of a patient. The plurality of images in a series similar to a movie that includes a first ultrasound image and a second ultrasound image with the second ultrasound image obtained at a different time than the first ultrasound image. The method further includes identifying, by a processor or a user via User input, a reference region at a first position in the first ultrasound image, the reference region including a reference element. In examples, the reference element is a pubis bone. A processor or a user, via user input, determines one or more regions of interest in the first ultrasound image. The one or more regions of interest including one or more target elements including a portion of a urethra, and the one or more regions of interest each have respective first positions defined relative to the reference region in the first ultrasound image. The processor determines (i) a second position of the reference region in the second image of the plurality of images, and (ii) a second position of the one or more regions of interest in the second ultrasound image. The processor further determines a change in position of the reference region from the first position of the reference region and the second position reference region, and a change in position of the one or more regions of interest from (i) the first position of the one or more regions of interest, (ii) the second position of the one or more regions of interest, and (iii) the change in position of the reference region. The processor then determines, from the change in position of the one or more regions of interest, movement of the portion of a urethra.

In examples, the method may further include tracking, via the processor, the motion of the one or more target elements from the change in position of the one or more regions of interest, such as tracking the motion of a target such as a portion of a urethra, uterus, perineum, vagina, pubis, or other pelvic floor element. The method may even further include determining, via the processor, an opening, closing, or stretching of the target from the change in the position of the one or more regions of interest.

In yet more examples, the processor may further determine (i) a first size and first orientation of the one or more regions of interest in the first ultrasound image, (ii) a second size and second orientation of the one or more regions of interest in the second ultrasound image, and (iii) at least one of a change in size of the one or more regions of interest from the first size and second size, and a change in orientation of the one or more regions of interest from the first orientation and second orientation. In such examples, the processor may determine, from the determined change of size or the determined change of orientation of the one or more regions of interest, a stretching, a compression, an opening, a closing of a portion of the target element, a velocity or acceleration of motion of independent regions of interest of the one or more regions of interest. Further, an order of movement of different pelvic floor structures, or different portions of a pelvic floor structure, may be determined from the motion of independent regions of interest. For example, the contraction of different portions of a urethra may be determined by the change in size and/or position of one or more regions of interest.

In another implementation, disclosed is a system for performing ultrasound motion tracking of a urethra. The system includes an ultrasound detector, a processor configured to execute machine readable instructions, and a non-transitory computer-readable memory having machine readable instructions stored thereon. When executed by the processor, the machine readable instructions cause the system to (a) obtain, by an ultrasound sensor, a plurality of ultrasound images of a region of tissue including a portion of a pelvis of a patient, the plurality of images including a first ultrasound image and a second ultrasound image, the second ultrasound image obtained at a different time than the first ultrasound image, (b) identify a reference region at a first position in the first ultrasound image, the reference region including a reference element, (c) identify, one or more regions of interest in the first ultrasound image, the one or more regions of interest including one or more target elements including a portion of a urethra, the one or more regions of interest each having a respective first position relative to the reference region in the first ultrasound image, (d) determine, by the processor, (i) a second position of the reference region in the second image of the plurality of images and (ii) a second position of the one or more regions of interest in the second ultrasound image, (e) determine, by the processor, a change in position of the reference region from the first position of the reference region and the second position of the reference region, (f) determine, by the processor, a change in position of the one or more regions of interest from (i) the first position of the one or more regions of interest, (ii) the second position of the one or more regions of interest, and (iii) the change in position of the reference region, and (g) determine, by the processor, from the change in position of the one or more regions of interest, movement of the portion of the urethra.

In examples, the machine readable instructions further cause the system to track, via the processor, the motion of the one or more target elements from the change in position of the one or more regions of interest, such as tracking the motion of a portion of the urethra. The machine readable instructions may even further cause the system to determine, via the processor, an opening, closing, or stretching of the urethra from the change in the position of the one or more regions of interest.

In yet more examples, the machine readable instructions may further cause the system to determine, by the processor, (i) a first size and first orientation of the one or more regions of interest in the first ultrasound image, (ii) a second size and second orientation of the one or more regions of interest in the second ultrasound image, and (iii) at least one of a change in size of the one or more regions of interest from the first size and second size, and a change in orientation of the one or more regions of interest from the first orientation and second orientation. In such examples, the machine readable instructions may further cause the processor to determine, from the determined change of size or the determined change of orientation of the one or more regions of interest, a stretching, a compression, an opening, or a closing of a portion of the target element.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Provided are techniques for tracking tissues and organs using machine vision processes. The specific application described utilizes machine vision to identify and track organs and tissues in the pelvic region of a patient. The disclosed methods and systems enable automated analysis and tracking of organs for medical diagnosis and treatment, such as for treatment of stress urinary incontinence (SUI) or pelvic organ prolapse (POP). Ultrasound (ultrasound) imaging is used to image the pelvic region of a patient, and machine vision then automatically tracks the movement of tissues and organs in real-time. Integrating computer vision with transperineal ultrasound enables real-time, or near real-time monitoring and capturing and quantitative analysis of dynamic movements of organs such as the urethra, vagina, pubis, perineal body, etc. The described methods and systems provide insight into the movements of organs and tissues enhancing the understanding and management of SUI and POP. Further, the disclosed methods allow for a deeper understanding of causes of SUI and POP and further advance the diagnostic and treatment of SUI and POP thereby improving patient outcomes and the overall quality of care. Further, the disclosed systems reduce the reliance on subjective judgment and skill of a practitioner in interpreting images and tracking of tissues while manipulating an ultrasound probe, providing a more systematic and standardized treatment for SUI and POP. While the disclosed examples provide motion tracking of portions of a urethra, it should be understood that the disclosed methods may be implemented in tracking other pelvic floor structures such as portions of a vagina, pelvis, rectum, perineal body, etc.

Figure 1:
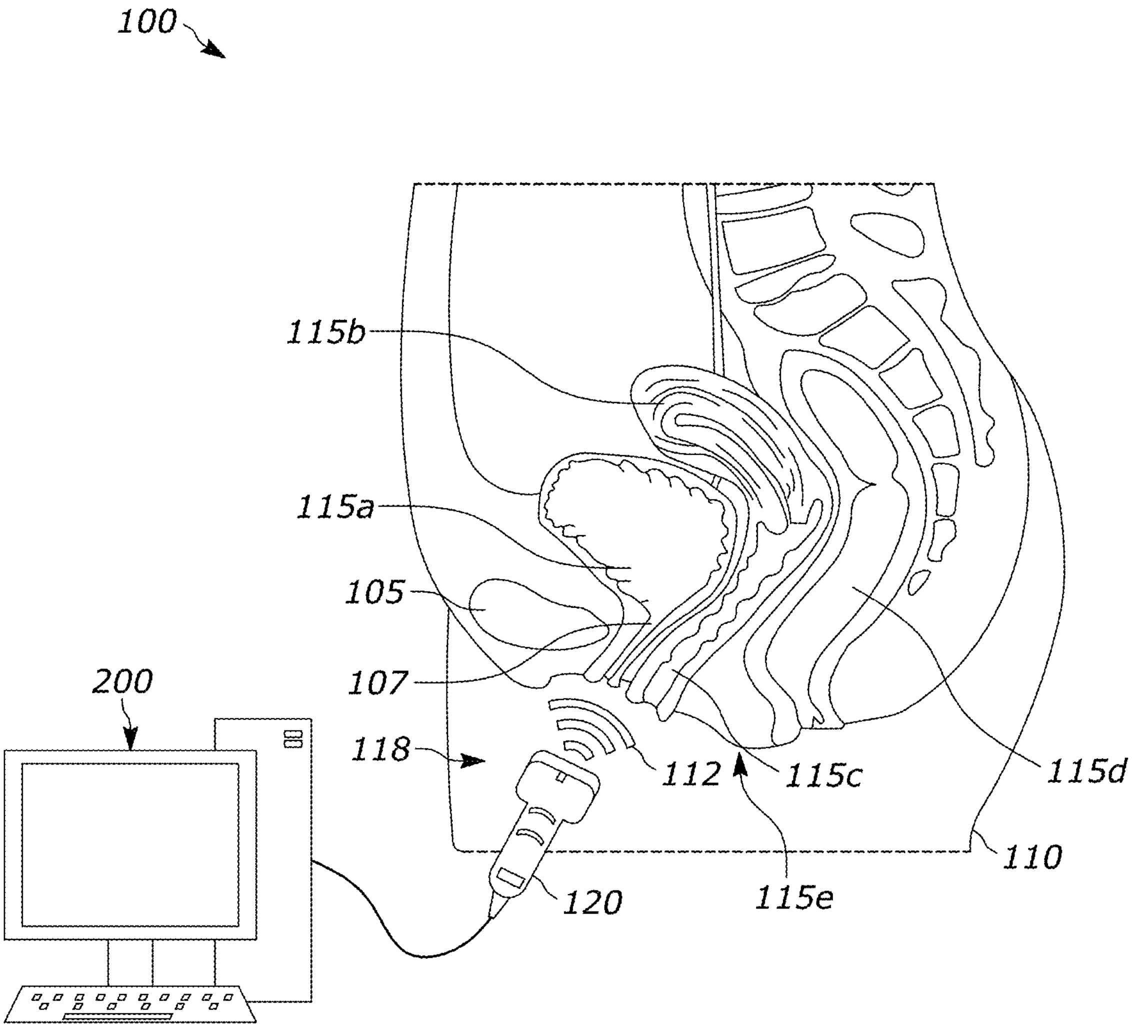
FIG. 1 is a schematic illustration of an example scenario for performing ultrasound (ultrasound) tracking of tissues and organs, in accordance with an example.

FIG. 1 is a schematic illustration of an example scenario 100 for performing ultrasound tracking of tissues and organs. In the example scenario 100 of FIG. 1, an ultrasound probe 120 is placed against the body 110 of a patient to provide ultrasound waves 112 to the body 110 and to detect reflected ultrasound vibrations. A gel, such as an ultrasound gel, may be applied to a portion of the body 110 and the ultrasound probe 120 may be placed against the portion of the body 110 having the ultrasound gel to increase the coupling of the ultrasound waves 112 into the body 110 of the patient. The ultrasound probe 120 may then receive reflected ultrasound vibrations to image tissues and organs inside of the body 110. In the illustrated example, the ultrasound probe 120 is positioned against the body 110 to image a pelvic region of the patient. The ultrasound probe may image one or more of a pubis 105, urethra 107, bladder 115*a*, uterus 115*b*, vagina 115*c*, rectum 115*d*, and perineal body 115*e*, among other tissues and/or organs.

As shown in FIG. 1, the ultrasound probe is positioned on the perineum in a mid-sagittal orientation for imaging. Movement of the ultrasound probe 120 relative to the pubic bone, as used herein as a solid reference for movement of the organs, during imaging also causes the positions of organs to change in the resultant ultrasound images. This artifact, which lacks diagnostic value, must be decoupled from the structural displacements and deformations of the organs during ultrasound imaging for performing motion tracking. To address this challenge, in line with previous research the symphysis pubis (SP) 105 is used as a stationary reference point due to its rigid structure. Therefore, as will be shown, urethral motion is tracked and monitored in relation to a coordinate system referenced to the pubis. This, in turn, enables the comparison of movements of structures adjacent to the pubis 105, and allows for the contextual registration of the movements or nearby organs and tissues.

Figure 2:
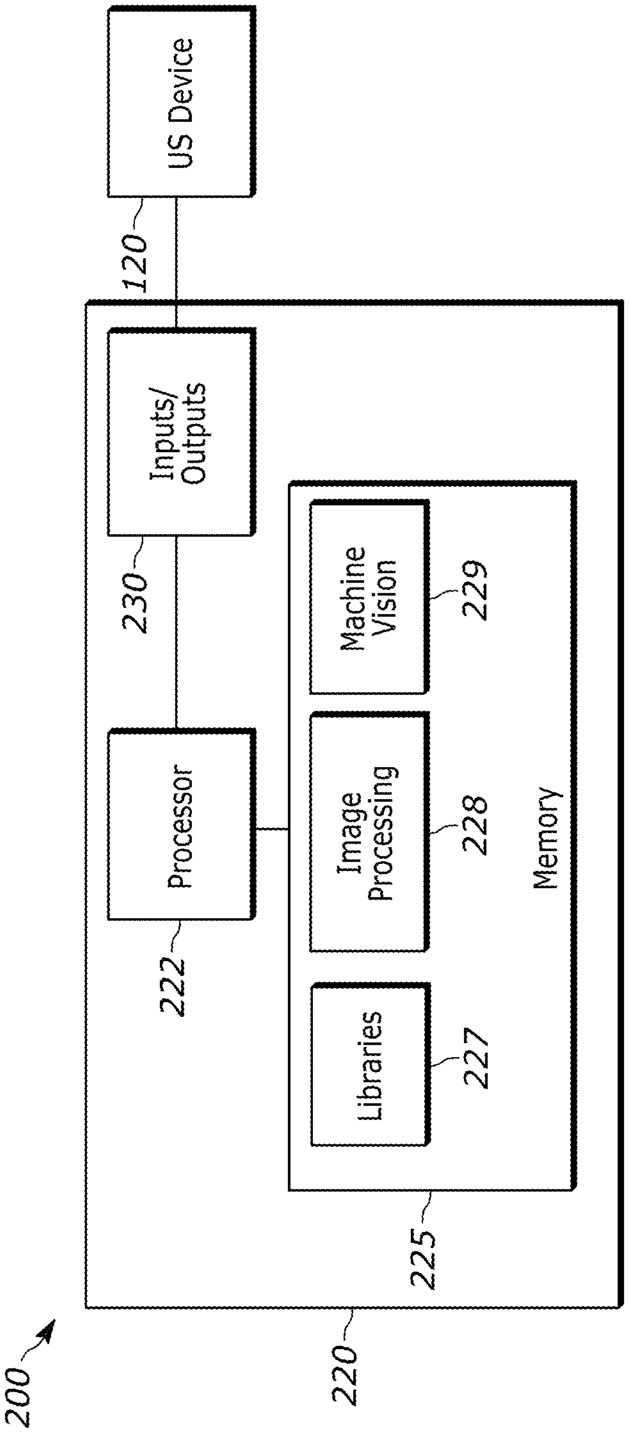
FIG. 2 is a block diagram of an example system for performing the ultrasound image and organ motion tracking methods, in accordance with an example.

The ultrasound probe 120 generates a signal indicative of the detected reflected ultrasound waves and provides the signal to one or more systems 200 for performing image processing, machine vision operations, and for displaying one or more ultrasound images and videos. FIG. 2 is a block diagram of an example system 200 for performing the ultrasound image and organ motion tracking methods described herein. The system 200 may be used to perform any of the methods disclosed herein. The system 200 includes one or more processors 222 that execute machine readable instructions for performing motion tracking according to the described methods. The processor may access one or more memories 225 to retrieve data, store data, and retrieve or store machine readable instructions. The one or more memories 225 may store one or more software or language libraries 227 (e.g. Python open source libraries, or other software and processing libraries), image processing algorithms 228, and machine vision processes 229. The image processing algorithms 228 may include image manipulations and transforms including but not limited to conversion to grayscale, histogram equalization, noise removal, etc. The machine vision processes 229 may include one or more motion tracking algorithms, such as one or more optical flow based algorithms.

The system 200 further includes one or more input/output ports 230 or devices. For example, the input/output ports 230 may include wired or wireless communication channels that receive or provide data to external networks, servers, and devices. The input/output ports 230 may include display devices such as monitors and touchscreens to provide images and video to a user. The input/output ports 230 may further include input devices such as one or more keyboards, mice, touchscreens, etc. In the example provided, the probe 120 provides data indicative of ultrasound images and video to the system 200 vie the input/output ports 230.

Figure 3:
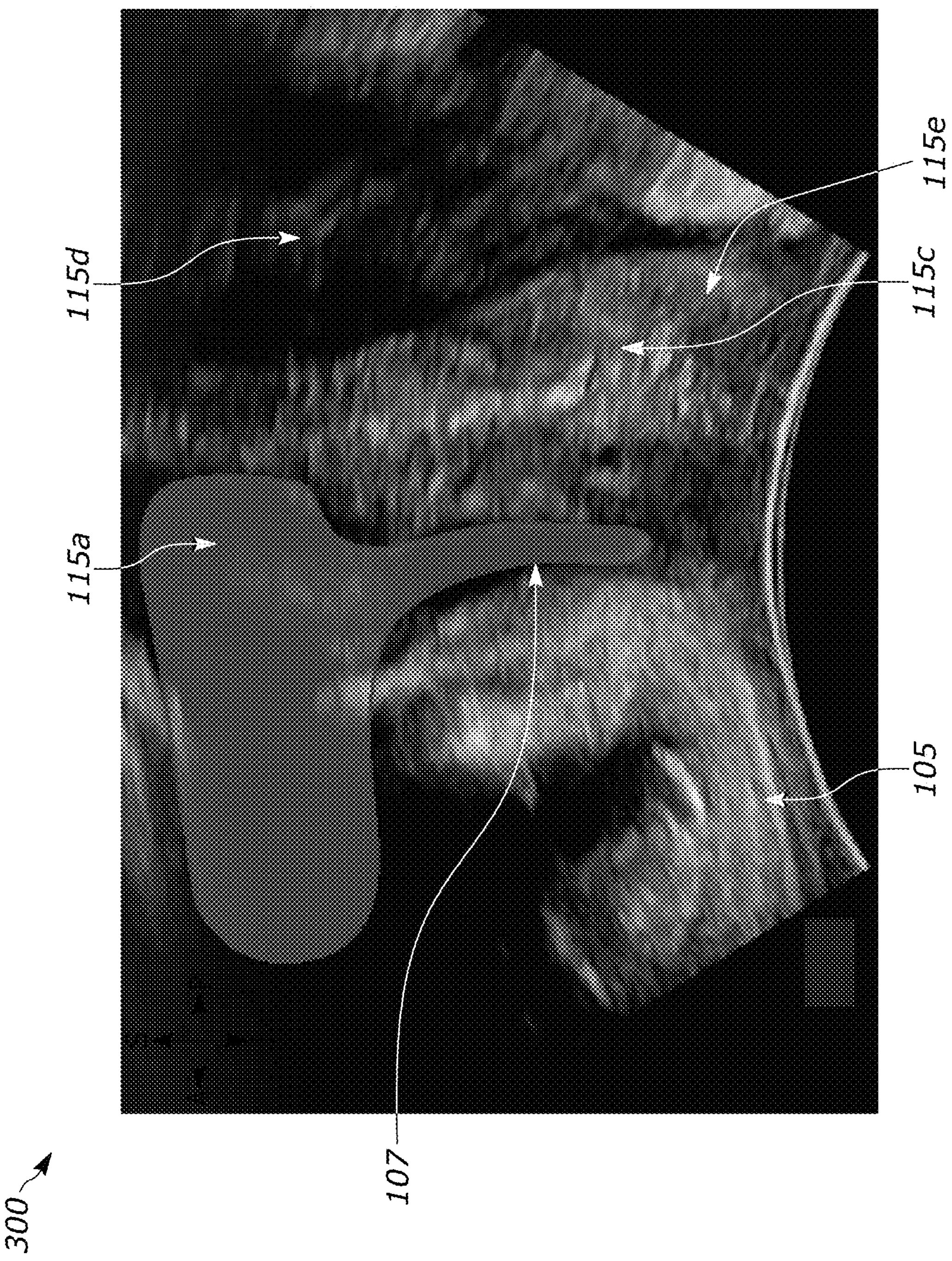
FIG. 3 is an example sagittal B-mode ultrasound image of the pubic region of a female patient taken according to the scenario of FIG. 1, and the system of FIG. 2, in accordance with an example.

FIG. 3 is an example sagittal B-mode ultrasound image 300 of the pubic region of a female patient taken according to the scenario 100 of FIG. 1, and the system 100 of FIG. 2. The image includes the pubis bone 105, urethra 107, bladder 115*a*, vagina 115*c*, and rectum 115*d*. The example image 300 of FIG. 3 shows the pelvic region which will be further used to illustrate the tissue and organ motion tracking using ultrasound imaging as described herein. The image 300 of FIG. 3 further includes a directional axis indicating the superior(S), inferior (I), posterior (P), and anterior (A) directions, as will be used herein.

Figure 4:
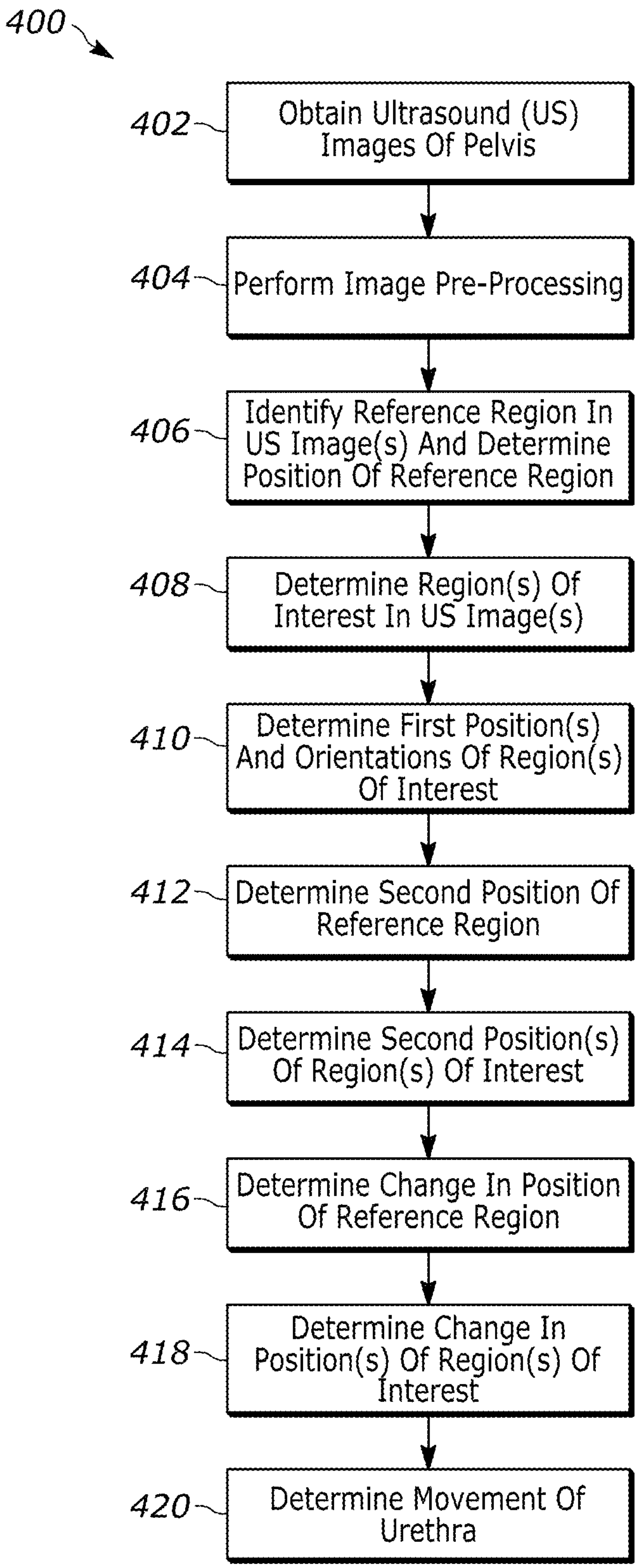
FIG. 4 is a flow diagram of a method for performing ultrasound motion tracking of an organ or tissue, in accordance with an example.

FIG. 4 is a flow diagram of a method 400 for performing ultrasound motion tracking of an organ or tissue, such as of a urethra. The method 400 may be performed using a system similar to those illustrated in FIGS. 1 and 2, and as such, the method 400 will be described with continued reference to elements of FIGS. 1 and 2 for clarity. The method 400 includes obtaining a plurality of ultrasound images of a region of tissue, such as a pelvis or pelvic region, of a patient, at block 402. The images may be obtained using a ultrasound probe, such as the probe 120. In examples, the ultrasound images may be obtained using a wearable device or tabletop ultrasound detector as well. The plurality of images includes at least two images taken at different times to determine movement of a urethra from the two different images. For simplicity, the method 400 is described herein with reference to only two ultrasound images, but it should be understood that the method 400 may be applied to any number of images for tracking the movement of a urethra.

For example, the ultrasound probe 120 may obtain a series of images over time to track the motion of a urethra. The ultrasound probe may obtain images at a rate of between 30 and 100 frames per second, 10 to 100 frames per second, 100 to 500 frames per second, 500 to 1000 frames per second, greater than 1000 frames per second or at another frequency for performing motion tracking. The method 400 may be used to track the motion of a urethra over seconds, minutes, tens of minutes, or longer.

The one or more processors 222 may then perform image preprocessing on one or more of the ultrasound images at block 404. The image preprocessing may include performing one or more image transformations, greyscale conversion, histogram equalizations, contrast enhancement, brightness normalization, background subtraction, thresholding, noise removal, etc. For example, the processor may first convert a ultrasound image to greyscale to reduce any color data to a single grey channel to simplify subsequent processing while retaining essential image data and information. A contrast limited adaptive histogram equalization (CLAHE) may then be applied to enhance image contrast. A CLAHE is typically effective in improving the visibility of features in medical imaging by normalizing the brightness and increasing contrast of medical images, such as ultrasound images.

Figure 5:
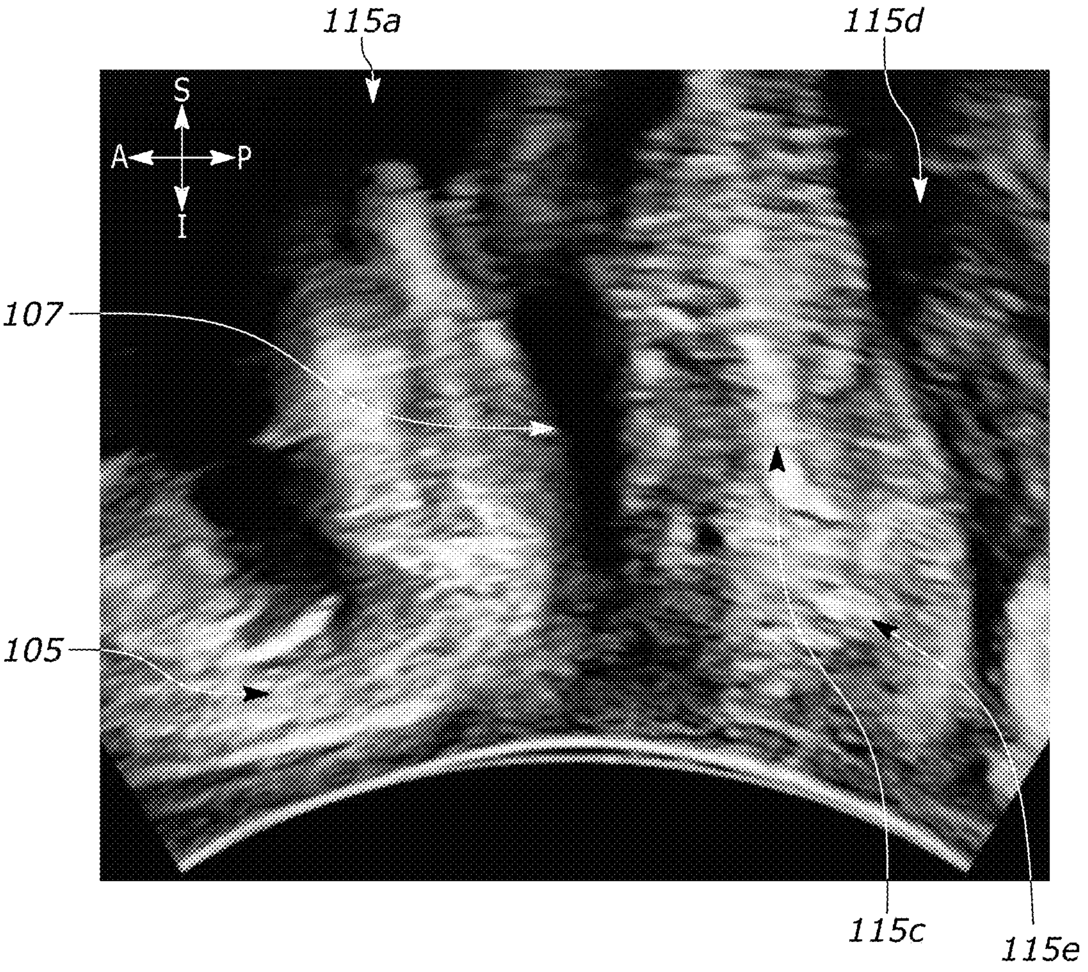
FIG. 5 is an example transperineal ultrasound image as may be obtained by the ultrasound probe for performing urethral motion tracking (as an example), in accordance with an example.
Figure 6A:
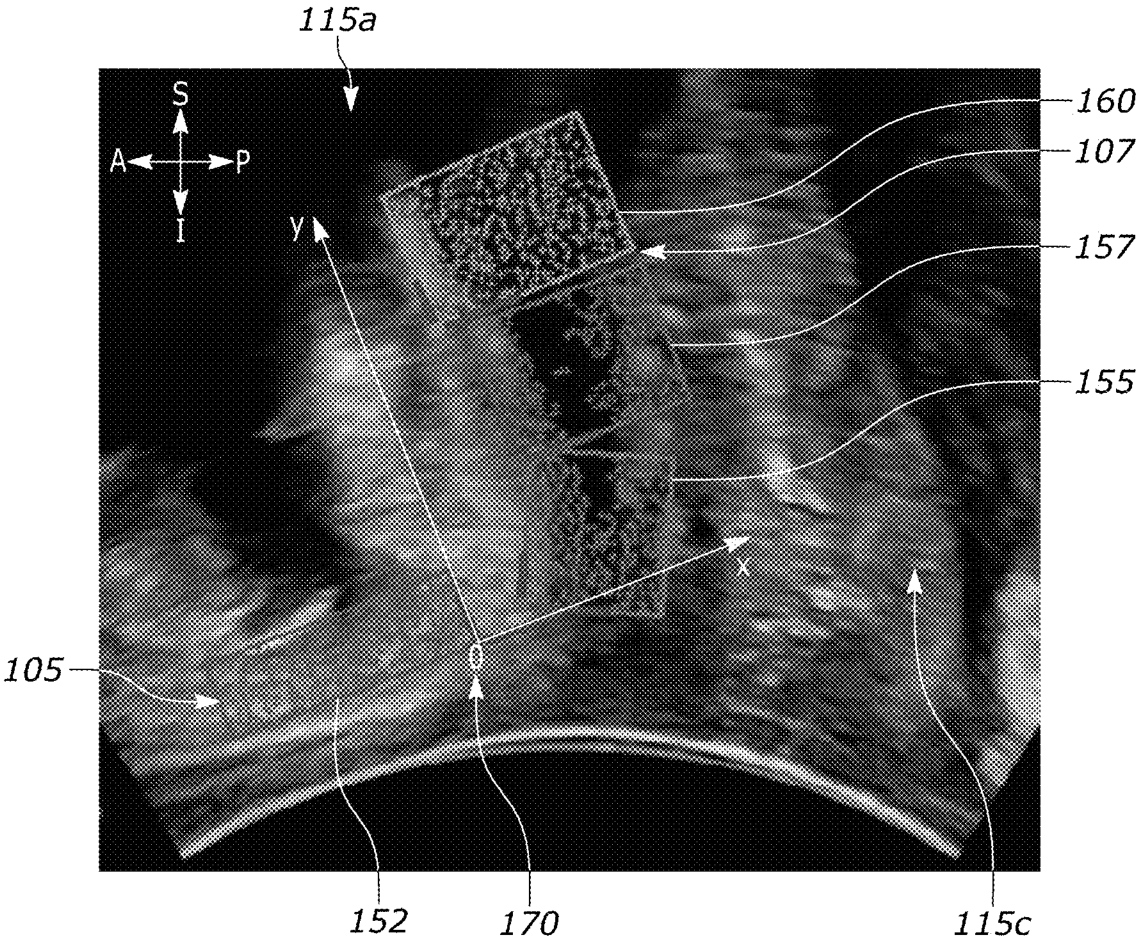
FIG. 6A is a first ultrasound image including a reference region being a rectangular region about the area of the image including the pubis, in accordance with an example.

FIG. 5 is an example transperineal ultrasound image as may be obtained by the ultrasound probe 120. The image is of pelvis region including the pubis 105, urethra 107, bladder 115*a*, vagina 115*c*, rectum 115*d*, perineal body 115*e*. At block 406 a reference region is identified in the first ultrasound image. FIG. 6A is a ultrasound image including a reference region 152 being a rectangular region about the area of the image including the pubis 105. The reference region 152 includes one or more reference elements that are to be tracked, and used as a coordinate reference for other regions of interest in the ultrasound image, described further herein. In the illustrated example, the pubis 105 (i.e., pubis bone) is used as the reference element and the reference region 152 is determined as a region including a portion of the pubis. As used herein, the word "portion" with reference to an anatomical structure includes at least part of the anatomical structure and may include the entire anatomical structure. The reference region may be identified by a processor, such as the one or more processor 222, of the reference region may be identified by a user via one or more user inputs or devices of the input/output ports 230. For example, the system 200 may display the first ultrasound image, and a user may use a mouse or touch screen to indicate the reference region. In the examples, the processor or a user identifies the reference element (e.g., pubis bone) and the processor further defines the reference region 152 to contain the reference element or a portion of the reference element. The processor 222 may determine the reference region 152 in the first image via performing image segmentation including one or more of, without limitation, edge detection, contrast analysis, thresholding, contouring, one or more morphological operations, or by applying another algorithm, machine vision, or imaging processing technique.

The processor then determines a position of the reference region 152 in the first image. The position may be determined based on pixel number or two-dimensional pixel address position in the image. In specific examples, the reference region may be defined based on coordinates of the four vertices of a rectangle or square indicative of the reference region 152 further based on a global coordinate system defined as bottom left corner of the image. Additionally, the processor can determine a size and orientation of the reference region 152 for example, a length and width of the rectangular reference region 152 of FIG. 6A, and an angular orientation of the reference region 152 in the image relative to the bottom right corner of the reference region 152, or on the global coordinates based on the bottom left pixel of the ultrasound image.

At block 408, the method 400 includes determining one or more regions of interest in the first ultrasound image. The one or more regions of interest include at least one target element in the first image which may be a tissue or organ of the patient, such as a urethra. FIG. 6A illustrates an example ultrasound image with three regions of interest indicative of different parts of the urethra 107. A first region of interest 155 is indicative of a distal portion of the urethra 107, a second region of interest 157 indicates a mid-urethra region, and a third region of interest 160 is indicative of a proximal urethral region. Each of the regions of interest 155, 157 and 160 are illustrated as rectangular boxes that surround a portion of the urethra 107. In examples, a processor may perform image processing or machine vision processes to determine the regions of interest, or a user may provide a user input to determine the regions of interest and the target elements. To determine the regions of interest, the processor 222 may perform image segmentation including one or more of, without limitation, edge detection, contrast analysis, thresholding, contouring, or one or more morphological operations in addition to other algorithms and image processing techniques.

In the example provided, each of the different portions of the urethra are used as the target elements for each respective region of interest. The processor may determine feature points in each of the regions of interest to identify one or more features or parts of a target element for tracking. For example, the feature points may be determined by specific tissue structures, image contrast regions indicating an interface between different organs or tissues. In examples, the feature points could be determined using corner detection algorithms. Corner detection algorithms essentially find points in an image where the intensity changes sharply in multiple directions. These feature points were found within each ROI. The feature points may be determined using software such as an OpenCV algorithm (e.g., goodFeaturesToTrack algorithm) that is based on corner detection and identifies regions in an image with large variation in intensity in all surrounding directions. In a first image, such as the first ultrasound image, a user may be prompted to provide an input indicative of one or more ROIs for the algorithm to then determine feature points to track in subsequent images. Additionally, it should be understood that while the reference region 152 and the regions of interest 155, 157, and 160 are illustrated as rectangles, the reference region 152 and the regions of interest 155, 157, and 160 may be any other shape indicative of respective reference elements and target elements for performing motion tracking of tissues or organs. For example, the each of the reference region 152, and regions of interest 155, 157, and 160 may independently be circles, ellipses, ovals, square, triangular, polygonal, an asymmetric shape, a freeform shape, or another two-dimensional geometric shape for indicating a region with a corresponding reference or target element. Rectangular regions of interest are implemented herein for simplicity and clarity of demonstration. Rectangular regions of interest maintain a consistent and simple description in position and orientation in a Cartesian coordinate system, as used herein.

The processor then determines first positions of each of the regions of interest 155, 157, and 160 in the first image at block 410. To determine positions of the regions of interest 155, 157, and 160 the processor may establish a coordinate axis or coordinate system based on the position and orientation of the reference region 152. As illustrated in FIG. 6A, the processor may establish a coordinate system 170 taking the bottom right vertex of the reference region 252 (i.e., at the inferior posterior of the pubis) as an origin, and establishing two axes parallel to the two adjacent sides of the rectangular reference region 152 at the origin, (e.g., a y-axis parallel to the width of the rectangle, and x-axis parallel to the length of the rectangle). The positions of each of the regions of interest 155, 157, and 160 may then be established by the bottom left corners of each of the regions of interest 155, 157, and 160 in the established coordinate system 170.

In examples, the processor may further determine a first orientation of each of the regions of interest 155, 157, and 160 relative to the origin O of the coordinate system 170. The orientation of each of the regions of interest 155, a157, and 160 may be determined by finding the transformation matric between the local coordinate system using the pubis reference region 152 and then determine the corners of each rectangular region of interest 155, 157, and 160 to determine each size and orientation. The processor may additionally determine a first size of each region of interest 155, 157, and 160, including different dimensions (e.g., length and width), in the first ultrasound image.

Figure 6B:
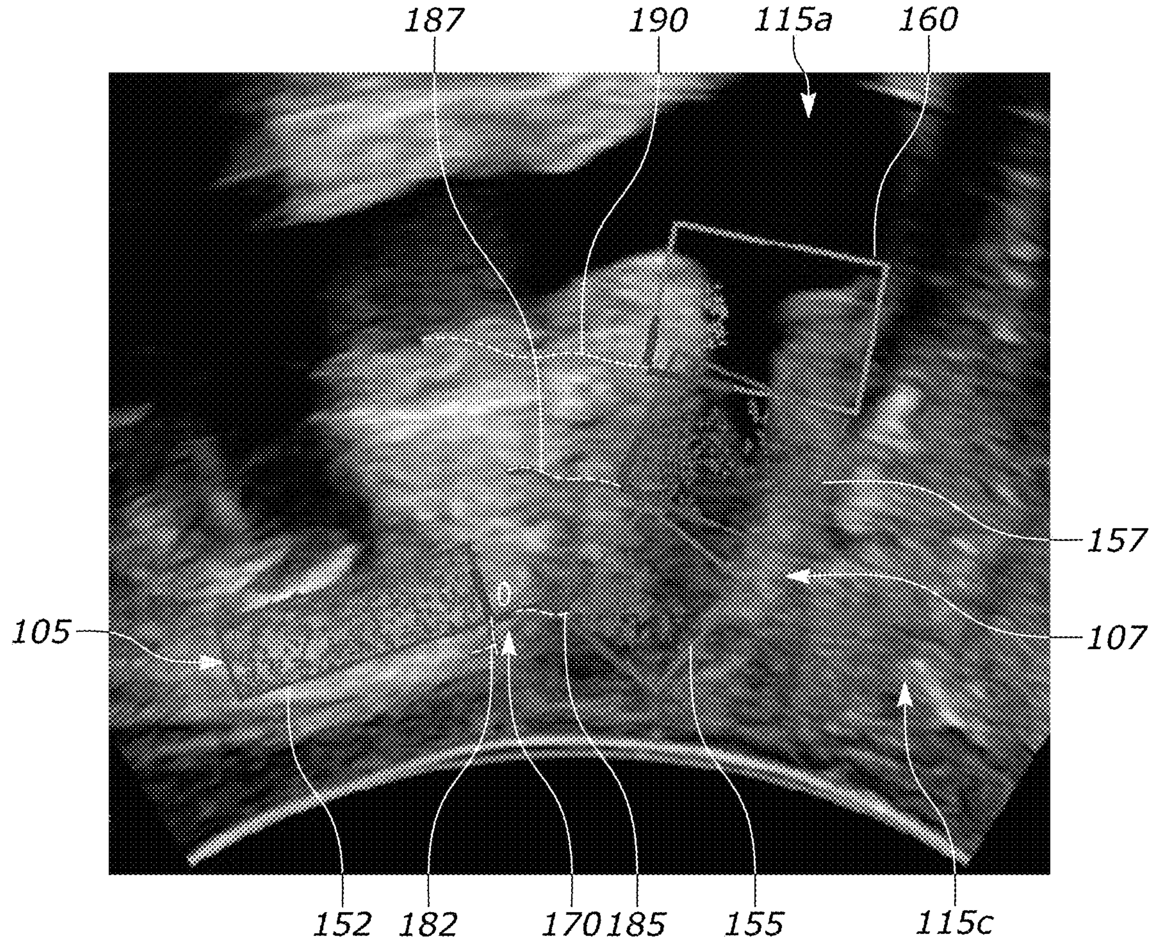
FIG. 6B is a second ultrasound image of the pelvic region of a patient taken at a different time than the first ultrasound image of FIG. 6A, in accordance with an example.

At block 412, the processor determines a second position of the reference region 152 in the second ultrasound image, at block 412. FIG. 6B is an ultrasound image of the pelvic region of a patient taken at a different time than the ultrasound image of FIG. 6A. In FIG. 6B, the urethra 107 and pelvis 105 have both moved relative to their positions and orientations in FIG. 6A. The processor determines the second position of the reference region 152, and re-establishes the same coordinate system 170 and origin O based on the position and orientation of the reference region 152 in the second ultrasound image. The processor then determines the regions of interest 155, 157, and 160 by performing image processing and identifying the distal, mid, and proximal urethra portions in the second ultrasound image. Once the regions of interest 155, 157, and 160 in the second ultrasound image are determined in the second ultrasound image, the processor determines second positions and orientations of each respective region of interest 155, 157, and 160 in the second ultrasound image in the established coordinate system 170, at block 412. In determining the second positions and orientations of each respective region of interest 155, 157, and 160, the processor may employ an optical flow algorithm such as the OpenCV algorithm calcOpticalFlowPyrLK, which is based on the Lucas-Kanade optical flow method. The optical flow algorithm estimates the movement and coordinates of a feature point from the first image into the position of the feature point in a second image. Therefore, the optical flow algorithm allows for determine the positions and movement of feature points between two consecutive ultrasound images as used herein.

The processor determines a change in position and orientation of the reference region 152 between the first and second ultrasound images at block 416. In determining the change in position, the processor determines a difference between the first position of the reference region 152 in the first ultrasound image, and the second position of the reference region 152 in the second ultrasound image. In implementation, the method 400 is performed on a plurality of ultrasound images including more than 2 ultrasound images, with the position and orientation of the reference region 152 being determine in each ultrasound image. FIG. 6B illustrates a reference region path 182 between the first position of the reference region 152 in the first ultrasound image, and ending at the second position of the reference region 152 illustrated in the second ultrasound image of FIG. 6B. The processor determined the reference region path 182 was from a plurality of ultrasound Images taken between the first ultrasound image of FIG. 6A, and the second ultrasound image of FIG. 6B. While the method 400 may be performed with only two ultrasound images, motion may be tracked via a path, such as the reference region path 182, by determining positions of reference regions and regions of interest in a plurality of ultrasound images over time.

At block 418, the processor determines corresponding changes of positions of the regions of interest 155, 157, and 160 from the first and second positions of the regions of interest 155, 157, and 160. As described above, and as illustrated in FIG. 6B, the positions of the regions of interest 155, 157, and 160 may be determined for a plurality of ultrasound images, and respective region of interest paths may be determined based on the positions of the regions of interest in each ultrasound image. For illustrative purposes, a first region of interest path 185, second Roi path 187, and third region of interest path 190 are illustrated respectively for the determined change in positions of the first, second, and third regions of interest 155, 157, and 160. To determine the paths of the reference region 152, and the regions of interest 155, 157, and 160, the processor may determine a geometric transformation matrix between the first and second ultrasound images, or generally between consecutive frames of a plurality of ultrasound images. One such example transformation matrix is a similarity transformation matrix given by, $$M = \begin{bmatrix} s\cdot\cos\theta & -s\cdot\sin\theta & t_x \\ s\cdot\sin\theta & s\cdot\cos\theta & t_y \end{bmatrix}. \qquad \text{EQ. 1}$$

The provided similarity transform matrix has four degrees of freedom; two translational $t_x$ and ty one rotational Θ, and a scaling factor s. The similarity transform matrix maintains the shape of an object in an image which preserves the angles of ROIs. In determining the transformation matric between two images, an OpenCV algorithm such as estimateAffinePartial2D may be implemented. Once the transformation matrix is determined, the processor then applies the transformation matrix to each of the regions of interest, applied at the vertices or positions of the regions of interest to determine the motion or paths of regions of interest from image to image.

The processor then determines the movement of organs or tissue, such as the urethra 107, based on the first and second positions, and the paths 185, 187, and 190 associated with respective regions of interest 155, 157, and 160, at block 420. Determining the paths of the various regions of interest 155, 157, and 160 over the plurality of ultrasound images enables motion tracking of various parts of the urethra 107. Additionally, by determining sizes and orientations of the regions of interest 155, 157, and 160, across multiple ultrasound images the processor may further determine stretching, opening, closing, bending and deformation of other pelvic floor structures. The method may further evaluate relative motion of tissues around a sub-region such as a sub-urethral tape or other similar procedure. Additionally, the method may further determine a velocity or acceleration of an organ or portion of tissue, or relative timing of movements of different portions of an organ or tissue such as movement or contractions of different portions of a urethra during an action such as a cough. For example, if a region of interest size increases over time, it can be determined that the portion of the urethra associated with the respective region of interest has stretched, or expanded (e.g., to open, allow fluid flow, etc.). The simultaneous monitoring and tracking of motion and stretching. Compression etc. of the urethra, for example, allows for improved accuracy and understanding in diagnosing and treating conditions such as SUI. Tracking movement of organs, (e.g. urethra, vagina, uterus), muscles (e.g. levator ani, bulbospongiosus) can be assessed using the disclosed method. These movements reflect the status of the fascial supports of the pelvic organs as well as the influence of muscles on these supports and are useful in determining the specific structural failures that cause organs to move abnormally. This information can prove useful in treatment planning to target interventions to the specific problem found in an individual.

The method 400 was demonstrated clinically on twenty female volunteers, aged 20 to 76 years with a mean age of 41.4±15.8 standard deviation. This is provided as an example a similar process could be used to track any of the pelvic organs or pelvic floor structures. Each of the volunteers were screened and indicated no history of prolapse, current cancer treatment, chronic urinary tract infections, organ transplants, prior pelvic area injuries or accidents, or recent pregnancy or childbirth within the prior three months. Further, the volunteers were each tested for current urinary tract infections. After confirming of the absence of urinary tract infections, B-mode ultrasound imaging was performed in the lithotomy position using a clinical scanners, Voluson® E10 (General Electric Healthcare) with a curvilinear C2-9-D probe, and Philips EPIQ® 5 W (Philips Healthcare, Bothell, WA, USA) with a linear eL 18-4 probe. The ultrasound image capture frame rate was set to the maximum possible rate (typically about 30 Hz±5 Hz), which depended on additional scanning parameters such as depth, field of view, and frequency. The imaging plane and depth was picked such that clear images of the bladder, urethra, and pubis could be obtained. The remaining scanning parameters (e.g., mechanical index, and gain) were set for optimum image quality and on a case-by-case basis for each volunteer.

The ultrasound probe was encased in a cover (Trojan Condoms, Church & Dwight Company, Ewing Township, NJ, USA) filled with ultrasound coupling gel (EcoVue Ultrasound Gel, A Division of HR® Pharmaceuticals, Inc., York, PA, USA). Additional ultrasound gel was applied over the cover before positioning it on the perineum in a mid-sagittal orientation, ensuring sufficient skin contact to maintain the location and orientation of the urogenital structures without causing distortion. During imaging, volunteers were instructed to perform a Valsalva maneuver on command. These processes were conducted by an obstetric and gynecology specialist. The ultrasound cine loops were stored as DICOM for offline analysis. Open source Python library was used to access and read the DICOM files.

Figure 7A:
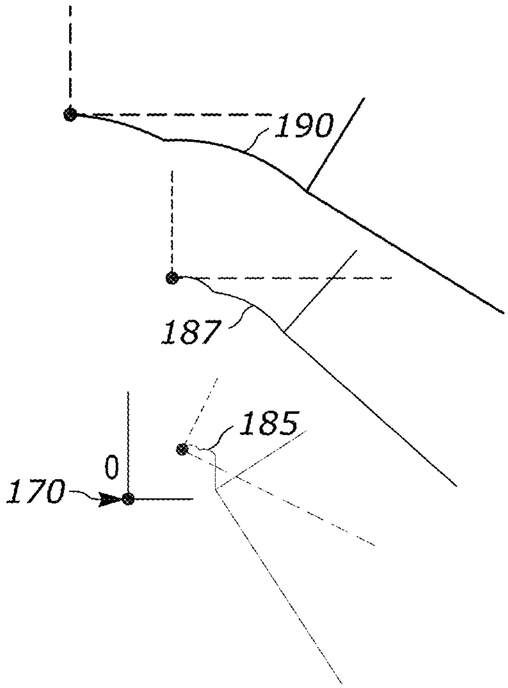
FIG. 7A is a diagram showing a coordinate system, first region of interest path, second region of interest path, and third region of interest path, in accordance with an example.
Figure 7B:
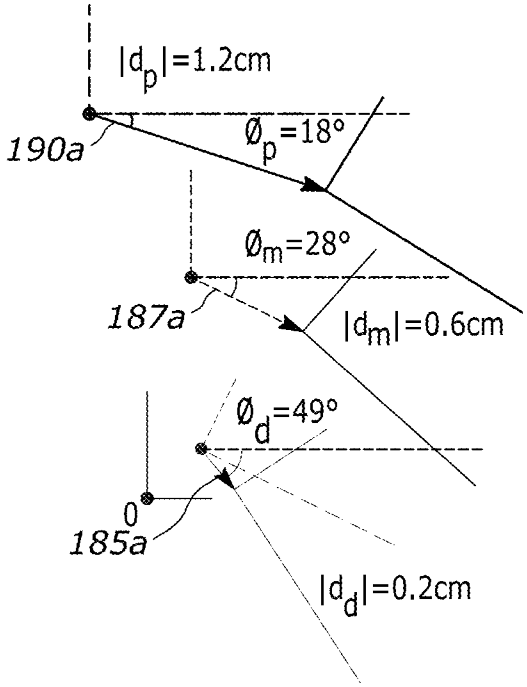
FIG. 7B is a diagram showing a determined displacement vector between the first and second ultrasound Images of FIGS. 6A and 6B, in accordance with an example.
Figure 7C:
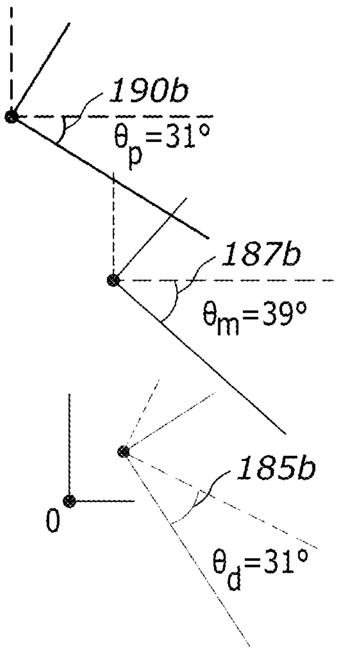
FIG. 7C is a diagram showing determined changes in orientations between the first and second ultrasound images of FIGS. 6A and 6B, in accordance with an example.

FIGS. 6A and 6B were taken as two sample ultrasound images from the images obtained during the clinical demonstration. Over 150 ultrasound images were obtained but more frames may be captured, or less to track motion of various organs and tissues during operation, or during an action for diagnosis, treatment, etc. The motion of three regions of interest of portions of a urethra, as previously described, was tracked using the method 400 of FIG. 4. FIG. 7A shows the coordinate system on the pubis 170, first region of interest path 185, second region of interest path 187, and third region of interest path 190. FIG. 7B shows the determined displacement vector between the first and second ultrasound Images of FIGS. 6A and 6B. The first displacement vector 185*a* of the first region of interest 155 is determine to have a magnitude of 0.2 cm and a direction 49° south of the horizontal coordinate axis, the second displacement vector 187*b* of the second region of interest 157 has a magnitude of 0.6 cm at a direction 28° south of the horizontal coordinate axis, and the third displacement vector 190*a* of the third region of interest 160 has a magnitude of 1.2 cm at a direction 18° south of the horizontal coordinate axis. FIG. 7C further shows the determined changes in orientations of the three regions of interest 155, 157, and 160 between the first and second ultrasound images. The first region of interest 155 exhibits a first rotation 185*b* of 31° counterclockwise, the second region of interest 157 exhibits a second rotation 187*b* of 39° counterclockwise, and the third region of interest 160 undergoes a third rotation 190*b* of 31° counterclockwise.

Figure 8A:
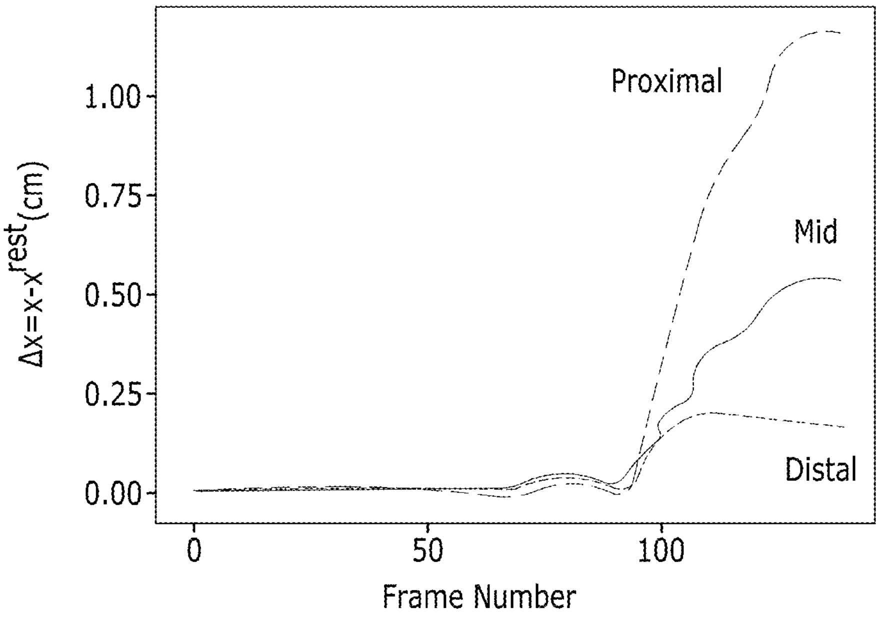
FIG. 8A is a plot of the x-coordinate displacement of three different urethral segments across a plurality of ultrasound images, in accordance with an example.
Figure 8B:
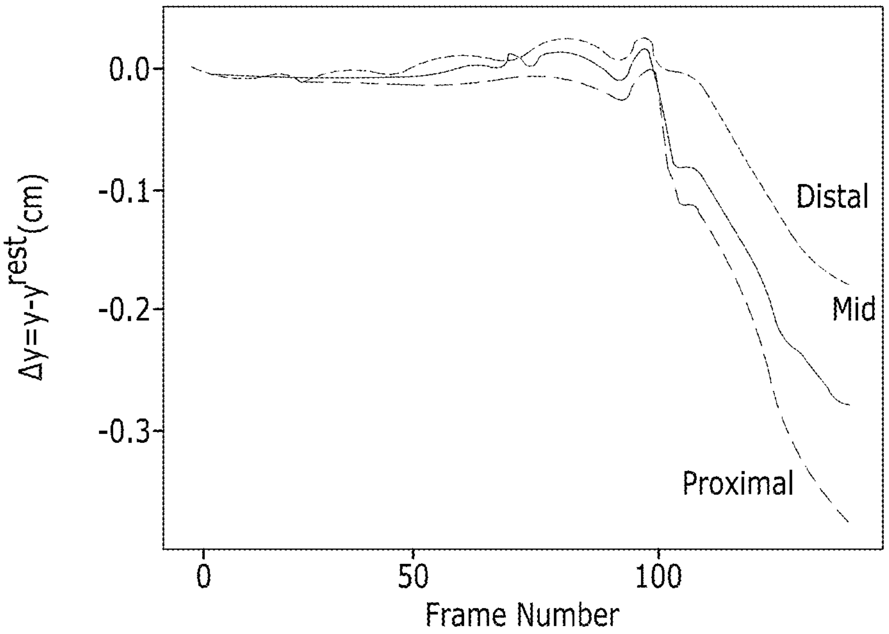
FIG. 8B is a plot of the y-coordinate displacement of three different urethral segments across a plurality of ultrasound images, in accordance with an example.

FIGS. 8A and 8B are plots of the x and y coordinate displacement, respectively, of the three different urethral segments of the three regions of interest 155, 157, and 160 across 150 ultrasound images with the first frame being the first ultrasound image of FIG. 6A, and the last frame being the second ultrasound image of FIG. 6B. The three different urethral portions do not move in tandem, in a same direction, or at a same amplitude. Tracking the three different regions of interest 155, 157, and 160 allows for motion tracking of different portions of the urethra to determine the absolute and relative motion of different parts of a urethra. The proximal urethra portion experiences the largest displacement in the x- and y-directions, followed by the mid and distal portions of the urethra. These types of motion patterns indicate a urethral “kinking” or “bending” phenomenon, as would be understood by a person of ordinary skill in the art. This increased understanding of the movement of different portions of the urethra may be beneficial in understanding, diagnosing, and providing treatment for conditions such as SUII. Further, more than three regions of interest could be used to further increased the tracking of portions of a urethra to finer detail and resolution.

Figure 9A:
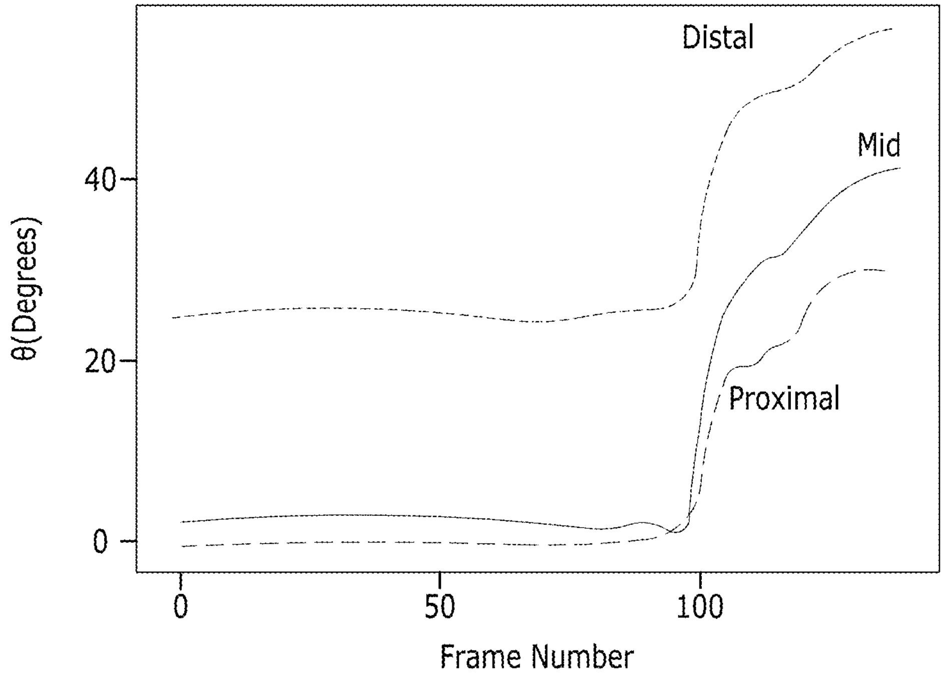
FIG. 9A is a plot of the relative angle of three different urethral segments across a plurality of ultrasound images, in accordance with an example.
Figure 9B:
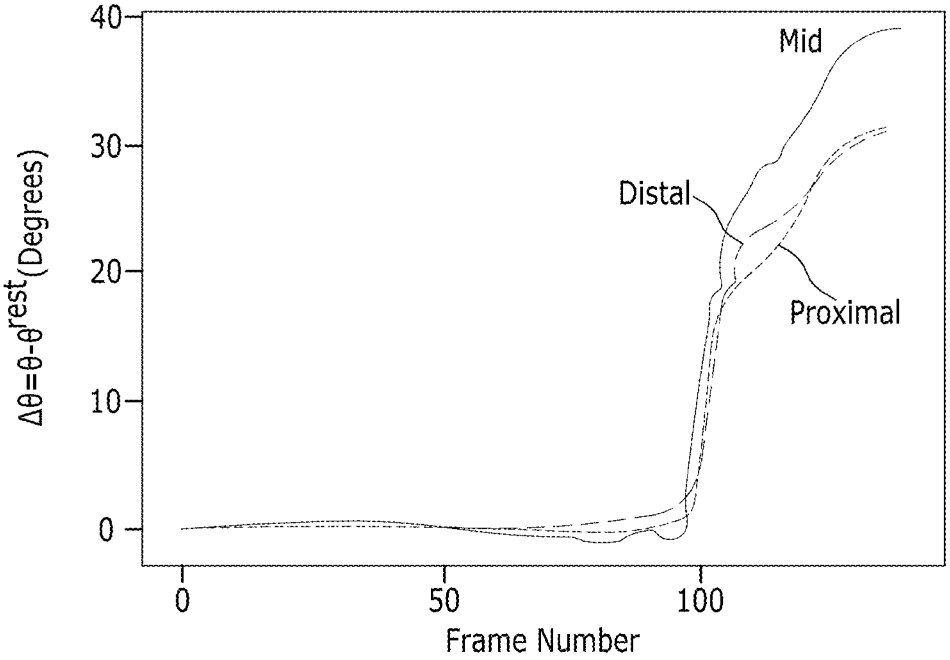
FIG. 9B is a plot of the rotation of three different urethral segments across a plurality of ultrasound images, in accordance with an example.

FIGS. 9A and 9B are plots of the relative angle, and total rotation of the three different urethral segments of the three corresponding regions of interest 155, 157, and 160 across 150 ultrasound images, with the first image being the first ultrasound image of FIG. 6A, and the last image being the second ultrasound image of FIG. 6B. The three different urethral portions exhibit different amounts of rotation during the movement of the urethra. The relative rotations of the three portions can further be used to understand stretching, opening, closing etc., of portions of the urethra. For example, the kinking phenomenon of the urethra is further demonstrated by the mid-portion of the urethra undergoing the most rotation. Observing both the varied rotation and displacement of the various segments of the urethra provides valuable insight into the biochemical behavior under different conditions (e.g., stress, relax, etc.).

Figure 10:
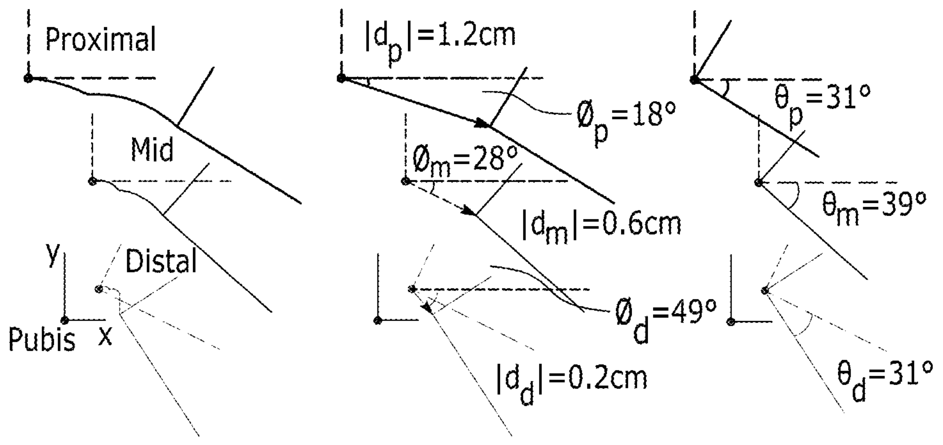
FIG. 10 is an illustration of an example urethral mobility report or summary of the movement of three portions of a urethra over time from the first ultrasound image of FIG. 6A, and the second ultrasound image of FIG. 6B.

FIG. 10 is an illustration of an example urethral mobility report or summary of the movement of three portions of a urethra over time from the first ultrasound image of FIG. 6A, and the second ultrasound image of FIG. 6B. The report includes graphical representations of the movement paths, displacement vectors, and rotations of the three regions of interest 155, 157, and 160, and further includes a table of values pertaining to metrics associated with the movement of the three regions of interest 155, 157, and 160. The mobility report provides a clear and succinct view of the various movement metrics to allow a practitioner to quickly analyze the urethral movement. Additionally, the urethral report of FIG. 10 may be provided to another system for further analysis or storing in a memory. The report of FIG. 10 is just one example of a report that may be generated for motion tracking and monitoring of a pelvic floor structure. For example, the movement of different regions (e.g., contraction, expansion, movement, etc.) of a vaginal canal, or rectum may be monitored for diagnosing or treating various conditions and a report may be generated that specifically reports metrics associated with those movements of organs and tissues. Additionally, reports of other movements, orientations, expansions, contractions, or tissues, organs, and regions of tissues and organs may be generated by the disclosed methods.

Additional Aspects

Aspect 1. A method for performing ultrasound motion tracking of pelvic floor structures, including the urethra, the method comprising: obtaining, by an ultrasound sensor, a plurality of ultrasound images of a region of tissue including a portion of a pelvis of a patient, the plurality of images including a first ultrasound image and a second ultrasound image, the second ultrasound image obtained at a different time than the first ultrasound image; identifying a reference region at a first position in the first ultrasound image, the reference region including a reference element; determining one or more regions of interest in the first ultrasound image, the one or more regions of interest including one or more target elements including a portion of a urethra, the one or more regions of interest each having respective first positions defined relative to the reference region in the first ultrasound image; determining, by the processor, (i) a second position of the reference region in the second image of the plurality of images, and (ii) a second position of the one or more regions of interest in the second ultrasound image; determining, by the processor, a change in position of the reference region from the first position of the reference region and the second position reference region; determining, by the processor, a change in position of the one or more regions of interest from (i) the first position of the one or more regions of interest, (ii) the second position of the one or more regions of interest, and (iii) the change in position of the reference region; and determining, by the processor, from the change in position of the one or more regions of interest, movement of the portion of the urethra.

Aspect 2. The method of Aspect 1, further comprising tracking, via the processor, the motion of the one or more target elements from the change in position of the one or more regions of interest.

Aspect 3. The method of either Aspect 1 or 2, wherein the reference element comprises a portion of a pubis bone.

Aspect 4. The method of any of Aspects 1 to 3, further comprising, determining, via the processor, an opening, closing, or stretching of the urethra or other pelvic floor tissues such as vagina, pubis, perineal body, rectum, etc. from the change in position of the one or more regions of interest.

Aspect 5. The method of any of Aspects 1 to 4, further comprising performing, by the processor, pre-processing on at least one image of the first ultrasound image and second ultrasound image.

Aspect 6. The method of Aspect 5, wherein the performing the pre-processing comprises one or more of performing a greyscale conversion, a histogram equalization, a contrast enhancement, a brightness normalization, noise removal and filtering, background subtraction, and thresholding.

Aspect 7. The method of any of Aspects 1 to 6, wherein identifying the reference region comprises receiving, via a user interface, a user identification of the reference region.

Aspect 8. The method of any of Aspects 1 to 7, wherein identifying the reference region comprises identifying, via the processor, the reference region via image segmentation Aspect 9. The method of any of Aspects 1 to 8, wherein identifying the one or more regions of interest comprises receiving, via a user interface, a user identification of the one or more regions of interest.

Aspect 10. The method of any of Aspects 1 to 9, wherein identifying the one or more regions of interest comprises identifying, via the processor, the one or more regions of interest via image segmentation.

Aspect 11. The method of any of Aspects 1 to 10, further comprising determining, via the processor, (i) a first size and first orientation of the one or more regions of interest in the first ultrasound image, (ii) a second size and second orientation of the one or more regions of interest in the second ultrasound image, and (iii) at least one of a change in size of the one or more regions of interest from the first size and second size, and a change in orientation of the one or more regions of interest from the first orientation and second orientation.

Aspect 12. The method of Aspect 11, further comprising determining, by the processor and from the determined change of size or the determined change of orientation of the one or more regions of interest, a stretching, a compression, an opening, or a closing of a portion of the target element, a deformation of pelvis floor structure, urethral shortening, urethral widening, funneling, etc.

Aspect 13. A system for performing ultrasound motion tracking of a urethra or other pelvic floor structure, the system comprising: an ultrasound detector; a processor configured to execute machine readable instructions; and a non-transitory computer-readable memory having machine readable instructions stored thereon, that when executed by the processor, cause the system to: obtain, by an ultrasound sensor, a plurality of ultrasound images of a region of tissue including a portion of a pelvis of a patient, the plurality of images including a first ultrasound image and a second ultrasound image, the second ultrasound image obtained at a different time than the first ultrasound image; identify a reference region at a first position in the first ultrasound image, the reference region including a reference element; identify, one or more regions of interest in the first ultrasound image, the one or more regions of interest including one or more target elements including a portion of a urethra, the one or more regions of interest each having a respective first position relative to the reference region in the first ultrasound image; determine, by the processor, (i) a second position of the reference region in the second image of the plurality of images, and (ii) a second position of the one or more regions of interest in the second ultrasound image; determine, by the processor, a change in position of the reference region from the first position of the reference region and the second position of the reference region; determine, by the processor, a change in position of the one or more regions of interest from (i) the first position of the one or more regions of interest, (ii) the second position of the one or more regions of interest, and (iii) the change in position of the reference region; and determine, by the processor, from the change in position of the one or more regions of interest, movement of the portion of the urethra.

Aspect 14. The system of Aspect 13, further comprising tracking, via the processor, the motion of the one or more target elements from the change in position of the one or more regions of interest.

Aspect 15. The system of either Aspect 13 or 14, wherein the reference element comprises a portion of a pubis bone.

Aspect 16. The system of any of Aspects 13 to 15, further comprising, determining, via the processor, an opening, closing, or stretching of the urethra or pelvic floor tissue including without limitation a vagina, pubis, perineal body, rectum, etc., from the change in position of the one or more regions of interest.

Aspect 17. The system of any of Aspects 13 to 26, further comprising performing, by the processor, pre-processing on at least one image of the first ultrasound image and second ultrasound image.

Aspect 18. The system of Aspect 17, wherein the performing the pre-processing comprises one or more of performing a greyscale conversion, a histogram equalization, a contrast enhancement, a brightness normalization, noise removal and filtering, background subtraction, thresholding, etc.

Aspect 19. The system of any of Aspects 13 to 18, wherein identifying the reference region comprises receiving, via a user interface, a user identification of the reference region.

Aspect 20. The system of any of Aspects 13 to 19, wherein identifying the reference region comprises identifying, via the processor, the reference region via image segmentation.

Aspect 21. The system of any of Aspects 13 to 20, wherein identifying the one or more regions of interest comprises receiving, via a user interface, a user identification of the one or more regions of interest.

Aspect 22. The system of any of Aspects 13 to 21, wherein identifying the reference region comprises identifying, via the processor, the one or more regions of interest via image segmentation.

Aspect 23. The system of any of Aspects 13 to 22, further comprising determining, via the processor, (i) a first size and first orientation of the one or more regions of interest in the first ultrasound image, (ii) a second size and second orientation of the one or more regions of interest in the second ultrasound image, and (iii) at least one of a change in size of the one or more regions of interest from the first size and second size, and a change in orientation of the one or more regions of interest from the first orientation and second orientation.

Aspect 24. The system of Aspect 23, further comprising determining, by the processor and from the determined change of size or the determined change of orientation of the one or more regions of interest, a stretching, a compression, an opening, or a closing of a portion of the target element.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the target matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion such as a Contrast Agent Injection System shown in FIG. 2) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A method for performing ultrasound motion tracking of pelvic floor structures, the method comprising:

obtaining, by an ultrasound sensor, a plurality of ultrasound images of a region of tissue including a portion of a pelvis of a patient, the plurality of images including a first ultrasound image and a second ultrasound image, the second ultrasound image obtained at a different time than the first ultrasound image;

identifying a reference region at a first position in the first ultrasound image, the reference region including a reference element;

determining one or more regions of interest in the first ultrasound image, the one or more regions of interest including one or more target elements including a portion of a pelvic floor structure, the one or more regions of interest each having respective first positions defined relative to the reference region in the first ultrasound image;

determining, by the processor, (i) a second position of the reference region in the second image of the plurality of images, and (ii) a second position of the one or more regions of interest in the second ultrasound image;

determining, by the processor, a change in position of the reference region from the first position of the reference region and the second position reference region;

determining, by the processor, a change in position of the one or more regions of interest from (i) the first position of the one or more regions of interest, (ii) the second position of the one or more regions of interest, and (iii) the change in position of the reference region; and determining, by the processor, from the change in position of the one or more regions of interest, movement of the portion of the pelvic floor structure.

2. The method of claim 1, further comprising tracking, via the processor, the motion of the one or more target elements from the change in position of the one or more regions of interest.

3. The method of claim 1, wherein the reference element comprises a portion of a pubis bone.

4. The method of claim 1, wherein the pelvic floor structure comprises a portion of a urethra, vagina, pubis, rectum, or perineal body.

5. The method of claim 1, further comprising, determining, via the processor, an opening, closing, or stretching of the pelvic floor structure from the change in position of the one or more regions of interest.

6. The method of claim 1, further comprising performing, by the processor, pre-processing on at least one image of the first ultrasound image and second ultrasound image, the preprocessing including one or more of performing a greyscale conversion, a histogram equalization, a contrast enhancement, a brightness normalization, noise removal, noise filtering, background subtraction, and thresholding.

7. The method of claim 1, wherein identifying the reference region comprises receiving, via a user interface, a user identification of the reference region.

8. The method of claim 1, wherein identifying the reference region comprises identifying, via the processor, the reference region via image segmentation.

9. The method of claim 1, wherein identifying the one or more regions of interest comprises receiving, via a user interface, a user identification of the one or more regions of interest.

10. The method of claim 1, wherein identifying the one or more regions of interest comprises identifying, via the processor, the one or more regions of interest via image segmentation.

11. The method of claim 1, further comprising determining, via the processor, (i) a first size and first orientation of the one or more regions of interest in the first ultrasound image, (ii) a second size and second orientation of the one or more regions of interest in the second ultrasound image, and (iii) at least one of a change in size of the one or more regions of interest from the first size and second size, and a change in orientation of the one or more regions of interest from the first orientation and second orientation.

12. The method of claim 11, further comprising determining, by the processor and from the determined change of size or the determined change of orientation of the one or more regions of interest, a stretching, a compression, an opening, or a closing of a portion of the target element, deformation, contraction, widening, or shortening of a pelvic floor structure.

13. A system for performing ultrasound motion tracking of a pelvic floor structure, the system comprising:

an ultrasound detector;

a processor configured to execute machine readable instructions; and a non-transitory computer-readable memory having machine readable instructions stored thereon, that when executed by the processor, cause the system to:

obtain, by an ultrasound sensor, a plurality of ultrasound images of a region of tissue including a portion of a pelvis of a patient, the plurality of images including a first ultrasound image and a second ultrasound image, the second ultrasound image obtained at a different time than the first ultrasound image;

identify a reference region at a first position in the first ultrasound image, the reference region including a reference element;

identify, one or more regions of interest in the first ultrasound image, the one or more regions of interest including one or more target elements including a portion of a pelvic floor structure, the one or more regions of interest each having a respective first position relative to the reference region in the first ultrasound image;

determine, by the processor, (i) a second position of the reference region in the second image of the plurality of images, and (ii) a second position of the one or more regions of interest in the second ultrasound image;

determine, by the processor, a change in position of the reference region from the first position of the reference region and the second position of the reference region;

determine, by the processor, a change in position of the one or more regions of interest from (i) the first position of the one or more regions of interest, (ii) the second position of the one or more regions of interest, and (iii) the change in position of the reference region; and determine, by the processor, from the change in position of the one or more regions of interest, movement of the portion of the pelvic floor structure.

14. The system of claim 13, further comprising tracking, via the processor, the motion of the one or more target elements from the change in position of the one or more regions of interest.

15. The system of claim 13, wherein the reference element comprises a portion of a pubis bone.

16. The system of claim 13, wherein the pelvic floor structure comprises a portion of a urethra, vagina, pubis, rectum, or perineal body.

17. The system of claim 13, further comprising, determining, via the processor, an opening, closing, or stretching of the pelvic floor structure from the change in position of the one or more regions of interest.

18. The system of claim 13, further comprising performing, by the processor, pre-processing on at least one image of the first ultrasound image and second ultrasound image, including one or more of performing a greyscale conversion, a histogram equalization, a contrast enhancement, a brightness normalization, noise removal, noise filtering, background subtraction, and thresholding.

19. The system of claim 13, wherein identifying the reference region comprises receiving, via a user interface, a user identification of the reference region.

20. The system of claim 13, wherein identifying the reference region comprises identifying, via the processor, the reference region via image segmentation.

21. The system of claim 13, wherein identifying the one or more regions of interest comprises receiving, via a user interface, a user identification of the one or more regions of interest.

22. The system of claim 13, wherein identifying the reference region comprises identifying, via the processor, the one or more regions of interest image segmentation.

23. The system of claim 13, further comprising determining, via the processor, (i) a first size and first orientation of the one or more regions of interest in the first ultrasound image, (ii) a second size and second orientation of the one or more regions of interest in the second ultrasound image, and (iii) at least one of a change in size of the one or more regions of interest from the first size and second size, and a change in orientation of the one or more regions of interest from the first orientation and second orientation.

24. The system of claim 23, further comprising determining, by the processor and from the determined change of size or the determined change of orientation of the one or more regions of interest, a stretching, a compression, an opening, or a closing of a portion of the target element, deformation, contraction, widening, or shortening of a pelvic floor structure.

* * * * *